(12) United States Patent
Hunter et al.

(10) Patent No.: US 8,172,790 B2
(45) Date of Patent: May 8, 2012

(54) NEEDLE-FREE INJECTOR DEVICE WITH AUTOLOADING CAPABILITY

(75) Inventors: Ian W. Hunter, Lincoln, MA (US); Brian D. Hemond, Lexington, MA (US); Dawn M. Wendell, Farmington, CT (US); Nora Catherine Hogan, Boston, MA (US); Andrew J. Taberner, Epsom (NZ); Nathan B. Ball, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 283 days.

(21) Appl. No.: 12/310,456

(22) PCT Filed: Aug. 31, 2007

(86) PCT No.: PCT/US2007/019247
§ 371 (c)(1),
(2), (4) Date: Jul. 2, 2009

(87) PCT Pub. No.: WO2008/027579
PCT Pub. Date: Mar. 6, 2008

(65) Prior Publication Data
US 2010/0016827 A1 Jan. 21, 2010

Related U.S. Application Data

(60) Provisional application No. 60/841,794, filed on Sep. 1, 2006.

(51) Int. Cl.
*A61M 5/30* (2006.01)

(52) U.S. Cl. .................................................. 604/68

(58) Field of Classification Search .................. 604/65, 604/66, 67, 68, 70, 71
See application file for complete search history.

(56) References Cited

U.S. PATENT DOCUMENTS

| 2,194,535 A | 3/1940 | Von Delden |
| 2,550,053 A | 4/1951 | Ferguson |
| 3,057,349 A | 10/1962 | Ismach |

(Continued)

FOREIGN PATENT DOCUMENTS

DE 201 05 183 U1 6/2002

(Continued)

OTHER PUBLICATIONS

International Search Report for Int'l Application No. PCT/US2006/004899; Date Mailed: Nov. 17, 2006, (5 pages).

(Continued)

*Primary Examiner* — Bhisma Mehta
(74) *Attorney, Agent, or Firm* — Hamilton, Brook, Smith, Reynolds, P.C.

(57) ABSTRACT

A needle-free transdermal transport device includes a chamber (900) for holding the substance to be injected, a nozzle (910) in fluid communication with the chamber, and a drug reservoir (950) for storing the substance to be transferred to the chamber. The needle-free transdermal transport device also includes a controllable magnet and coil electromagnetic actuator (242) in communication with the chamber. The actuator receives an electrical input and generates in response a force. The force then causes a needle-free transfer of the substance from the chamber to the biological body. The force is variable responsive to variations in the received input during actuation. The actuator draws the substance from the drug reservoir or alternatively, the substance can be pressurized from the drug reservoir into the chamber by a pressure source.

19 Claims, 9 Drawing Sheets

U.S. PATENT DOCUMENTS

| | | | |
|---|---|---|---|
| 3,788,315 A | | 1/1974 | Laurens |
| 3,923,060 A | | 12/1975 | Ellinwood, Jr. |
| 4,108,177 A | | 8/1978 | Pistor |
| 4,552,559 A | | 11/1985 | Donaldson et al. |
| 4,592,742 A | | 6/1986 | Landau |
| 5,074,843 A | | 12/1991 | Dalto et al. |
| 5,116,313 A | | 5/1992 | McGregor |
| 5,347,186 A | | 9/1994 | Konotchick |
| 5,354,273 A | | 10/1994 | Hagen |
| 5,389,085 A | | 2/1995 | D'Alessio et al. |
| 5,405,614 A | | 4/1995 | D'Angelo et al. |
| 5,425,715 A | * | 6/1995 | Dalling et al. ............... 604/136 |
| 5,505,697 A | | 4/1996 | McKinnon, Jr. et al. |
| 5,533,995 A | | 7/1996 | Corish et al. |
| 5,578,495 A | | 11/1996 | Wilks |
| 5,611,784 A | * | 3/1997 | Barresi et al. ............... 604/211 |
| 6,030,399 A | | 2/2000 | Ignotz et al. |
| 6,090,790 A | | 7/2000 | Eriksson |
| 6,126,629 A | | 10/2000 | Perkins |
| 6,132,385 A | | 10/2000 | Vain |
| 6,203,521 B1 | | 3/2001 | Menne et al. |
| 6,288,519 B1 | | 9/2001 | Peele |
| 6,317,630 B1 | | 11/2001 | Gross et al. |
| 6,319,230 B1 | | 11/2001 | Palasis et al. |
| 6,939,323 B2 | | 9/2005 | Angel et al. |
| 7,032,443 B2 | | 4/2006 | Moser |
| 7,425,204 B2 | | 9/2008 | Angel et al. |
| 2002/0055729 A1 | | 5/2002 | Goll |
| 2002/0095124 A1 | | 7/2002 | Palasis et al. |
| 2003/0065306 A1 | | 4/2003 | Grund et al. |
| 2004/0106893 A1 | | 6/2004 | Hunter |
| 2004/0106894 A1 | | 6/2004 | Hunter et al. |
| 2004/0143213 A1 | | 7/2004 | Hunter et al. |
| 2004/0260234 A1 | | 12/2004 | Srinivasan et al. |
| 2006/0258986 A1 | | 11/2006 | Hunter et al. |
| 2007/0191758 A1 | | 8/2007 | Hunter et al. |

FOREIGN PATENT DOCUMENTS

| | | |
|---|---|---|
| DE | 101 46 535 A | 4/2003 |
| EP | 0 599 940 B1 | 12/1997 |
| EP | 0 834 330 A2 | 4/1998 |
| EP | 1 020 200 A2 | 7/2000 |
| GB | 2307860 A | 6/1997 |
| WO | WO 93/03779 A1 | 3/1993 |
| WO | WO 95/07722 A1 | 3/1995 |
| WO | WO 01/37907 A1 | 5/2001 |
| WO | WO 03/039635 A2 | 5/2003 |
| WO | WO 03/068296 A2 | 8/2003 |
| WO | WO 03/086510 A1 | 10/2003 |
| WO | WO 2004/021882 A2 | 3/2004 |
| WO | WO 2004/022138 A2 | 3/2004 |
| WO | WO 2004/071936 A2 | 8/2004 |
| WO | WO 2004/101025 A2 | 11/2004 |
| WO | WO 2004/112871 A1 | 12/2004 |
| WO | WO 2006/086720 A2 | 8/2006 |
| WO | WO 2006/086774 A2 | 8/2006 |
| WO | WO 2008/027579 A1 | 3/2008 |

OTHER PUBLICATIONS

Written Opinion for Int'l Application No. PCT/US2006/004899; Date Mailed: Nov. 17, 2006, (10 pages).

International Preliminary Report of Patentability for Int'l Application No. PCT/US2006/004899; Date Mailed: Aug. 14, 2007, (11 pages).

International Search Report for Int'l Application No. PCT/US2006/005043; Date Mailed: Nov. 16, 2006, (5 pages).

Written Opinion for Int'l Application No. PCT/US2006/005043; Date Mailed: Nov. 16, 2006, (10 pages).

International Preliminary Report of Patentability for Int'l Application No. PCT/US2006/005043; Date Mailed: Aug. 14, 2007, (11 pages).

International Search Report for Int'l Application No. PCT/US2007/019247; Date Mailed: Dec. 4, 2007, (5 pages).

Written Opinion for Int'l Application No. PCT/US2007/019247; Date Mailed: Dec. 4, 2007, (7 pages).

International Preliminary Report of Patentability for Int'l Application No. PCT/US2007/019247; Date Mailed: Mar. 3, 2009, (8 pages).

* cited by examiner

NEEDLE-FREE INJECTOR DEVICE WITH AUTOLOADING CAPABILITY

RELATED APPLICATIONS

This application is the U.S. National Stage of International Application No. PCT/US2007/019247, filed Aug. 31, 2007, published in English, and claims the benefit of U.S. Provisional Application No. 60/841,794, filed on Sep. 1, 2006. The entire teachings of the above applications are incorporated herein by reference in their entirety.

BACKGROUND OF THE INVENTION

Needle-free delivery of a liquid drug can be achieved by pressurizing the drug and rapidly ejecting it through a narrow orifice, thereby creating a high speed jet which can readily penetrate skin and the underlying tissue. Typically, this technique requires a pressure of 10 to 60 MPa to be developed on the drug over a few milliseconds, and then maintained for up to 100 ms.

Needle-free drug delivery has several advantages over needle-based delivery, particularly when many successive injections are required or injection discomfort is a major concern. However, in order for needle-free injector devices to become ubiquitous, they need to be controllable, repeatable, portable, and inexpensive.

Until very recently, most of the portable devices developed for jet injection have relied on springs or compressed gases to store and then rapidly release energy in order to create the high pressures required. The use of shape memory alloys and magnetic drives has also been proposed for actuating in jet injectors.

SUMMARY

Most portable injector devices allow for very little control of the pressure applied to the drug during the time course of injection. A needle-free transdermal transport device with a controllable magnet and coil electromagnetic actuator allows for more control in transferring a substance across a surface of a biological body. The needle-free transdermal transport device includes a chamber for holding the substance to be injected. It further includes a nozzle in fluid communication with the chamber. Further, a drug reservoir stores the substance to be transferred to the chamber.

The needle-free transdermal transport device also includes a controllable magnet and coil electromagnetic actuator in communication with the chamber. The actuator receives an electrical input and generates in response a force. The force then causes a needle-free transfer of the substance from the chamber to the biological body. The force is variable responsive to variations in the received input during actuation. The actuator also draws the substance from the drug reservoir. The drawing is precisely controlled to move the substance to the chamber for injection.

The needle-free transdermal transport device can further include a pressure source for automatically pressurizing the substance in the drug reservoir to transfer it from the drug reservoir into the chamber. The actuator can include a moving coil assembly and a stationary magnet, or alternatively a moving magnet assembly and stationary coil assembly.

In the case of a moving coil and stationary magnet, the force generated within the coil assembly is dynamically variable according to variations in the received electrical input. Variations in the received electrical input correspond to feedback.

In one embodiment, the controllable electromagnetic actuator is bi-directional, and generates a positive force responsive to a first electrical input and a negative force responsive to a second electrical input. The electromagnetic actuator forces the substance through a nozzle producing a jet having sufficient velocity to pierce the surface of the biological body.

The needle-free transdermal transport device can further include a rechargeable power source, used in production of the electrical input.

The needle-free transdermal transport device a first valve between the pressure source and the drug reservoir. This first valve can be a solenoid valve. Further, the device can include a check-valve between the drug reservoir and the chamber. The device can further include a pressure sensor for sensing the pressure inside the chamber.

The device can further include a piston for pushing the substance out of the nozzle for delivery. A position sensor can monitor the position of the piston within the needle-free injector. In one embodiment, a processor can automatically tailor the position of the actuator according to feedback from the position sensor.

The device can also include a servo-controller in electrical communication with the controllable electromagnetic actuator, where the servo-controller provided the electrical input. The device can provide a plurality of independent needle-free transfers, where each transfer occurs in rapid succession with respect to a preceding transfer.

The device can further include an automatically controlled flip-cap on the nozzle, where the flip cap closes during loading of the chamber with the substance and opens during injection of the substance.

In another embodiment, the needle-free transdermal transport device includes a controllable magnet and coil electromagnetic actuator in communication with the chamber. The actuator receives an electrical input and generates in response a force. The force then causes a needle-free transfer of the substance from the chamber to the biological body. The force is variable responsive to variations in the received input during actuation. The substance to be injected is pressurized from a drug reservoir into the chamber by a pressure source.

A method of transferring a substance across a surface of a body includes the step of drawing the substance from a drug reservoir with a controllable magnet and coil electromagnetic actuator, where the drawing is precisely controlled to move the substance to a chamber of a needle-free injector. An electrical input is then applied to the actuator. A mechanical force is then produced by the actuator, where the force corresponds to the electrical input. Finally, the mechanical force is applied to the chamber that is coupled at one end to a nozzle. The mechanical force produces a pressure within the chamber. The force causes a needle-free transfer of the substance from the chamber to the biological body and the force is variable in response to variations in the received input during actuation.

An alternative method of transferring a substance across a surface of a body includes the step of pressurizing the substance from a drug reservoir into a chamber with a pressure source. An electrical input is then applied to a controllable coil and magnet electromagnetic actuator. A mechanical force is then produced by the actuator, where the force corresponds to the electrical input. Finally, the mechanical force is applied to the chamber that is coupled at one end to a nozzle. The mechanical force produces a pressure within the chamber. The force causes a needle-free transfer of the substance from the chamber to the biological body and the force is variable in response to variations in the received input during actuation.

Another method of transferring a substance across a surface of a body includes sensing the position of a piston within a cylinder of a needle-free injector. Then an electrical input is applied to a controllable magnet and coil electromagnetic actuator. A mechanical force is then produced by the actuator, where the force corresponds to the electrical input. Finally, the mechanical force is applied to the chamber that is coupled at one end to a nozzle. The mechanical force produces a pressure within the chamber. The force causes a needle-free transfer of the substance from the chamber to the biological body and the force is variable in response to variations in the received input during actuation.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

A superior approach to jet drug delivery is to store energy in electrical form, and impose a time-varying pressure-profile on the drug volume through the use of a monitored and servo-controlled electromechanical actuator. Monitoring force, pressure, or delivered drug volume allows the time course and volume of drug delivery to be tightly defined, and controlled in real-time.

Linear Lorentz-force (voice-coil) actuators are a form of electromechanical motors that can generate the high force, pressure, and stroke length required for jet drug delivery. Their inherent bi-directionality allows the applied pressure to be controlled and even reversed when necessary. However, commercially available voice-coil actuators that meet the power demands of this application are typically too large, heavy and expensive to be appropriate for a portable handheld needle-free injector device. Lorentz-force actuators are relatively inexpensive, compact, and light weight, allowing them to serve as the force generator in a portable and reusable needle-free injector system.

Lorentz-force actuators are further described in U.S. application Ser. No. 11/352,916 filed on Feb. 10, 2006, claiming the benefit of U.S. Provisional Application No. 60/652,483 filed on Feb. 11, 2005, U.S. application Ser. No. 11/351,887 filed on Feb. 10, 2006 claiming the benefit of U.S. Provisional Application No. 60/652,483 filed on Feb. 11, 2005, and U.S. application Ser. No. 11/354,279 which is a continuation of U.S. application Ser. No. 11/352,916 filed on Feb. 10, 2006, which claims the benefit of U.S. Provisional Application No. 60/652,483, filed on Feb. 11, 2005, all herein incorporated by reference in their entirety.

With the recent advent of comparatively inexpensive high energy density rare-earth magnets, (Nd—Fe—B) it is now possible to construct quite compact, yet sufficiently powerful voice coil actuators for jet drug delivery. Additionally, high energy and power density capacitors allow sufficient energy to be locally stored and delivered rapidly to effect a needle-free injection in a portable, handheld device.

Figure 1:
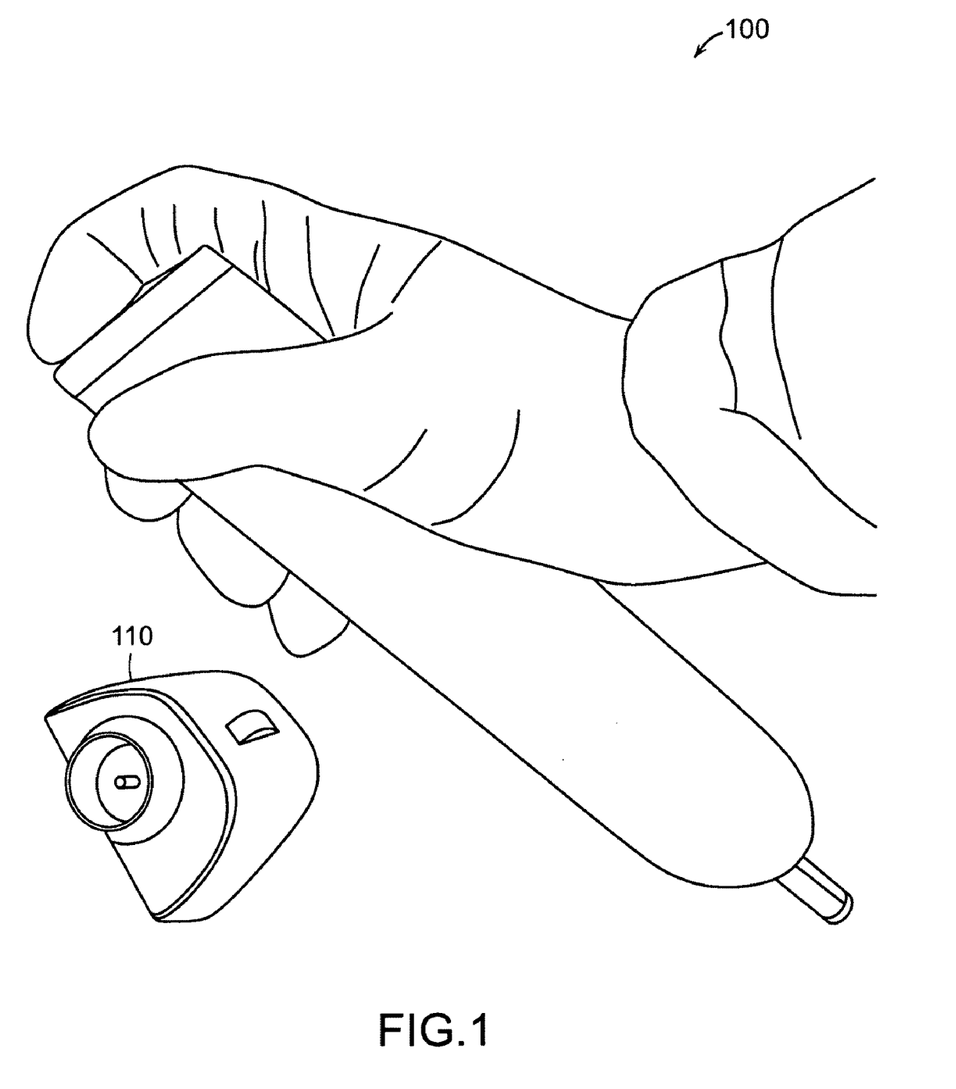
FIG. 1 shows a portable needle-free injector and a recharging dock.

One embodiment of a portable needle-free injector device 100 is show in FIG. 1. The portable system 100 includes a needle-free injector system based on a custom voice-coil actuator, with a mass of about 0.5 kg. It can be recharged from a battery powered dock 110 (approximately 90 seconds recharge time). Alternatively, it can be recharged from a high voltage supply (approximately 1 second recharge time) and provides a single injection per recharge (not shown). Alternatively or in addition, any suitable charging means can be used to recharge the device.

The portable needle-free injector delivery device 100 can include a disposable commercially-available 300 µl needle-free injector ampule (for example, Injex™ Ampule, part #100100) attached directly to a custom-designed moving-coil Lorentz-force actuator.

Figure 2:
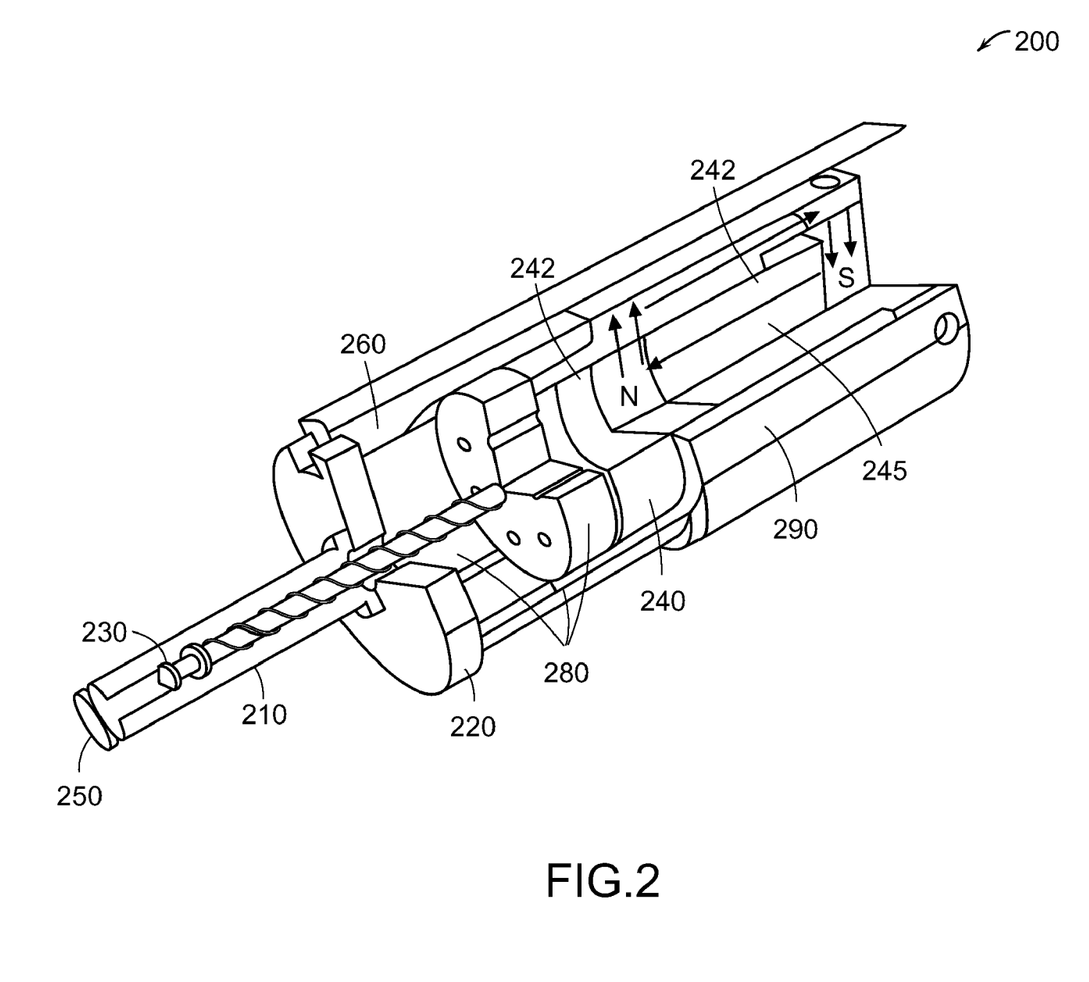
FIG. 2 is a partial cut-away perspective diagram of an embodiment of a controllable needle-free injector device.

An embodiment of a needle-free injector device 200 is shown as a partial cut-away in FIG. 2. A needle-free syringe 210 is screwed into a front plate 220 of the needle-free injector device 200, and a syringe piston 230 is captured by a snap-fitting on the front of a moving coil 240. The syringe-piston 230 may have a rubber tip or be made of any suitable material. The moving coil 240 can be constrained by the main shaft of the device and the bearings 280.

The drug or substance can then be gently drawn into the syringe 210 by a motor (not shown), from a vial, with the aid of a vial adapter (for example, Injex™ vial adaptor, part #200203.) Alternatively, the syringe 210 can be pre-filled or manually filled prior to loading into the device 200. An orifice 250 at the tip of the syringe 210 has a diameter of 165 µm; the diameter of the piston 230 is approximately 3.16 mm.

In this embodiment, the moving voice coil 240 includes 582 turns of 360 µm diameter enameled copper wire wound (using a custom-made coil winding machine) six layers deep on a thin-walled former. The voice-coil former is machined from Acetal copolymer (rather than a metal such as aluminum) in order to minimize the moving mass (approximately 50 g), and to avoid the drag caused by induced eddy currents in a conducting former. The total DC resistance of the coil is 11.3Ω. It can be understood, that variations of these specific parameters are possible.

As the voice coil 240 moves in a motor 242 (as described below), it slides freely and smoothly on the inside of the same steel extrusion from which a magnetic circuit 245 is constructed. This approach obviates the need for the extra size and length of a separate linear bearing.

Flexible electrical connections are made to the moving coil 240 by means of plastic-laminated copper ribbons. The position of the voice coil actuator 240 is monitored by a 10 k Ω linear potentiometer (i.e., position sensor 260) with >1 kHz bandwidth, although alternate potentiometers are possible. The potentiometer/position sensor 260 can alternatively be positioned in the back of the motor 242, or on any suitable position on the motor 242. The needle-free injector 200 can also include a steel casing 290.

Thus, the injector 200 includes the Lorentz-force (voice-coil) motor 242 made of the magnets 245 and moving coil 240. In summary, this motor is an electromagnetic actuator which drives a piston of a needle-free injector to inject the drug from the needle-free injector into the patient's skin. There are two primary types: moving-magnet and moving coil. The latter is far more common. Though both can be used effectively in needle-free injector devices, a moving coil type has been described in the embodiment of FIG. 2.

The linear Lorentz-force (voice-coil) motor 242 as described in FIG. 2 is commonly utilized today in audio speakers. For example, a commercial voice-coil actuator, a BEI Kimco Magnetics model LA25-42-000A was used in the design of the needle-free injector 200 of FIG. 2.

Figure 3A:
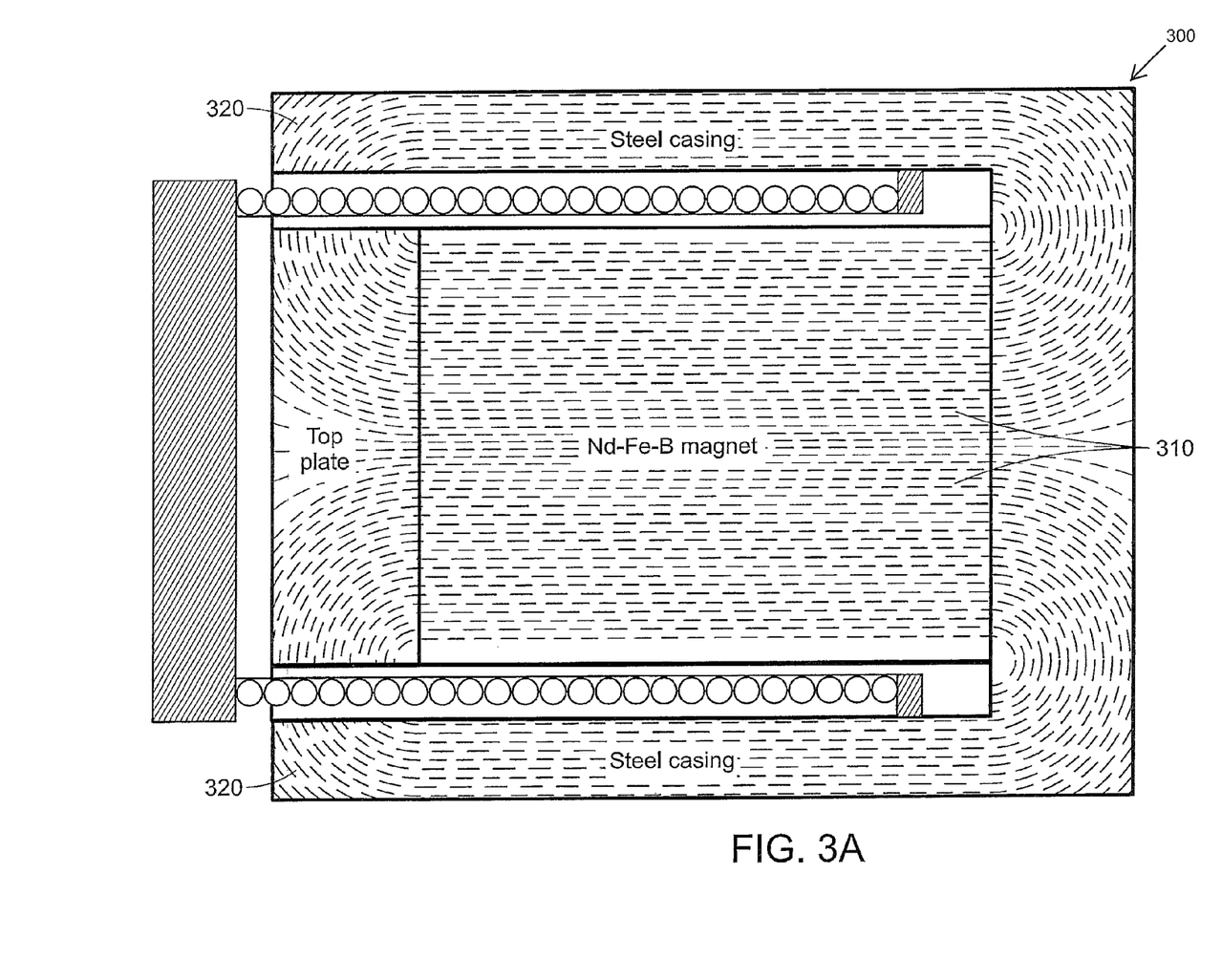
FIGS. 3A, 3B, and 3C illustrate components of a magnetic circuit for use in the needle-free injector device of FIG. 2.

An embodiment of a magnetic circuit 300 used in a voice-coil motor is shown in FIG. 3A. The magnetic circuit includes two 0.4 MN/m 2 (50 MGOe) NdFeB magnets 310 inserted into a 1026 carbon steel casing 320. The casing 320 may alternatively be any suitable material. Advantageously, this design avoids stray magnetic field leaking from the device due to magnetic flux saturation in the steel. The magnetic flux density in the field gap was approximately 0.6 T.

Figure 3B:
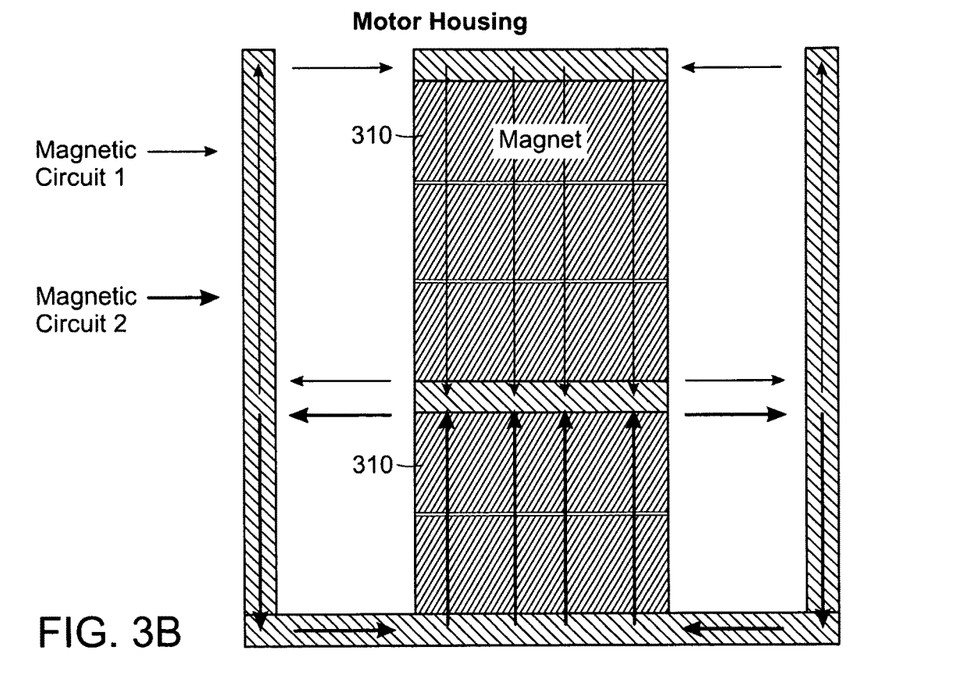
Figure 3C:
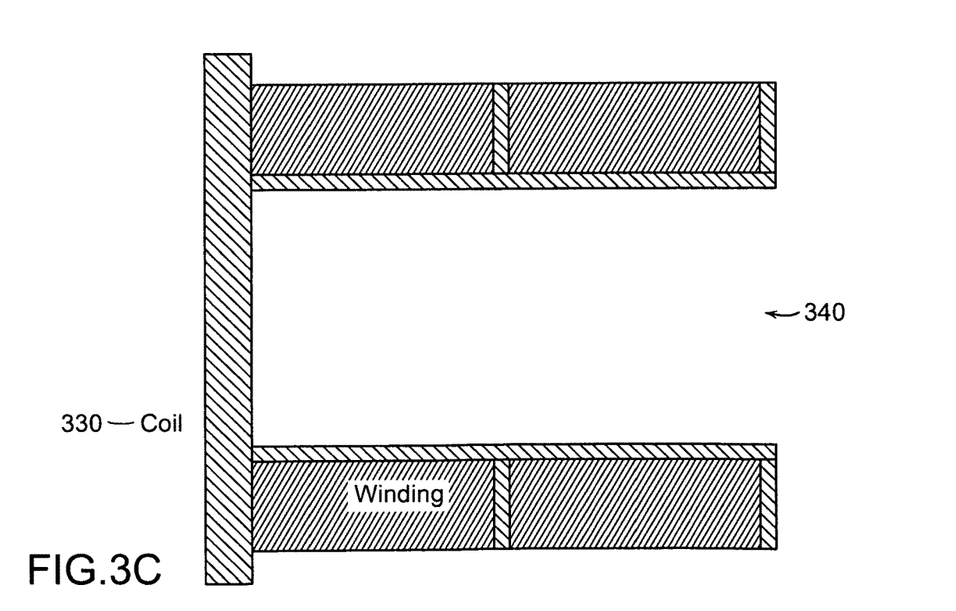

Further detail of the magnetic circuit of the voice-coil motor is shown in FIGS. 3B and 3C. FIG. 3B shows an embodiment of the motor housing. A pair of opposing coils 330 and 340 are wound on the same bobbin and slid over a shaft comprised of two sets of opposing permanent magnets 310 as shown in FIG. 3C. The field from the upper set of three magnets is squeezed by the opposing field from the lower set of magnets. This field crosses an air gap to the motor housing and crosses the second air gap on the way back to the opposite pole of the upper set of magnets 310. Likewise, the lower set of magnets produce a field that crosses the middle air gap, but can flow through the housing on the return pathway. Thus, the field at the center gap is quite strong, and somewhat weaker at the upper gap The windings of the coil 340 and 330, as shown in FIG. 3C, are located such that they are intersected by the two air gaps. A current applied to the windings causes a force to be generated between the coil bobbin and housing, thus causing the bobbin to move.

In the portable needle-free injector device 200, the voice coil motor 242 is energized from a low inductance electrolytic capacitor. The bench-top test system is driven by a 4 kW linear power amplifier, controlled by a PC-based data acquisition and control system running in National Instruments Labview™ 7.1. This approach readily allows for a variety of voltage waveforms to be tested on the device, while its current and displacement performance is monitored and recorded.

The performance of the voice-coil motor 242 has been quantified by measuring its frequency response, step response and its open-loop repeatability. Additionally the efficacy was confirmed by injecting red dye into post-mortem guinea-pig tissue.

Figure 4:
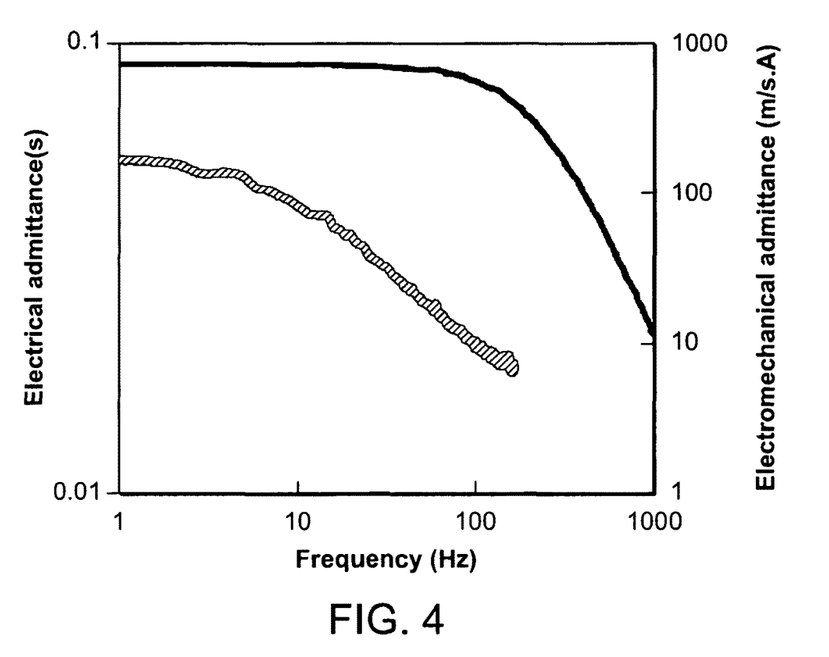
FIG. 4 is a graph showing the frequency response of one embodiment of a voice coil motor.

The frequency dependent properties of the voice-coil motor can be quantified in terms of the magnitude of its electrical and electromechanical admittance as shown in FIG. 4. The electrical admittance (formed by the series resistance and inductance of the voice coil) is approximately that of a first order R-L filter (R=11.3 &, L=4.6 mH) with a cut-off frequency of approximately 400 Hz. The no-load electromechanical admittance (velocity per unit of sinusoidal current) provides a measure of the voice coil motor's responsiveness to driving current.

The force sensitivity of a voice coil motor quantifies the relationship between voice coil current and developed force. For a pure Lorentz-force motor, force sensitivity is the product of the magnetic flux density and the total length of coil in the magnetic field. In a preferred embodiment, the voice coil motor has a force sensitivity of 10.8±0.5 N/A averaged along the length of its stroke, reaching a peak of 11.5 N/A at mid-stroke.

Figure 5:
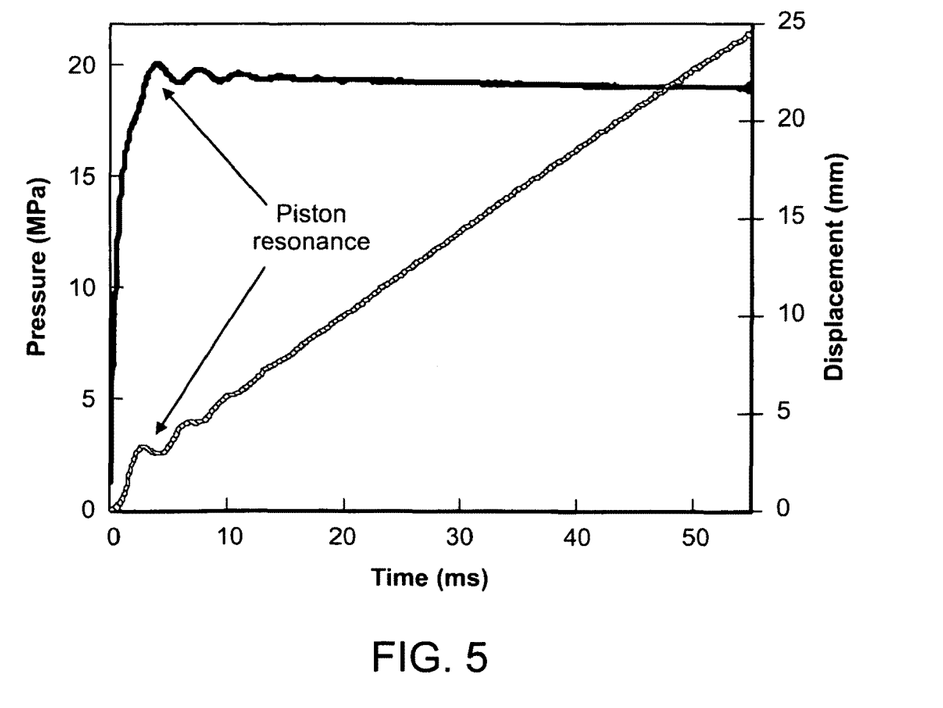
FIG. 5 is a graph illustrating the pressure and displacement step response during an injection with one embodiment of a needle-free injector.

By applying a brief 200 V potential to the voice coil, more than 200 N of force can be imposed upon the syringe piston 230. This generates fluid pressure of approximately 20 MPa (comparable to that generated by conventional, commercially-available jet injectors) which is sufficient to effect jet injection of a 250 µL volume of drug as shown in FIG. 5. The instantaneous power consumed by the voice coil under these conditions is approximately 4 kW. However, because the injection is completed in a mere 50 ms, there is advantageously negligible heating of the coil (<10° C.).

In a voice-coil motor, the force produced is directly proportional to the current through the motor's coils. Thus, given a sufficiently controllable power supply, the force versus the time profile of the motor and therefore the pressure versus time profile of the ejected drug can be advantageously tailored to produce the best possible injection for a given skin type and injection liquid.

The electrical time constant of the voice coil current is 0.4 ms. As the current increases, force rapidly develops on the piston 230, compressing its rubber tip against the fluid, and accelerating the fluid through the orifice 250. The resonance of the rubber piston tip decays after a few milliseconds, and the piston 230 reaches a steady state velocity which appears to be mostly determined by the mechanics of the fluid flow through the orifice 250. Bernoulli's equation for inviscid, steady, incompressible flow gives the relationship between velocity and pressure as:

$$v = \sqrt{\frac{2P}{\rho}}$$

Thus, the needle-free injector is advantageously electrically controlled so that approximately every millisecond of the injection profile (speed of fluid exiting the nozzle as determined by the pressure in the drug reservoir or ampule) can be programmed. Alternatively, various time increments of an injection profile can be programmed as desired. Because the injector has integral pressure and position sensors (to be described in FIG. 9) the pressure in the fluid can be measured before it exits the nozzle of the injector.

Figure 6:
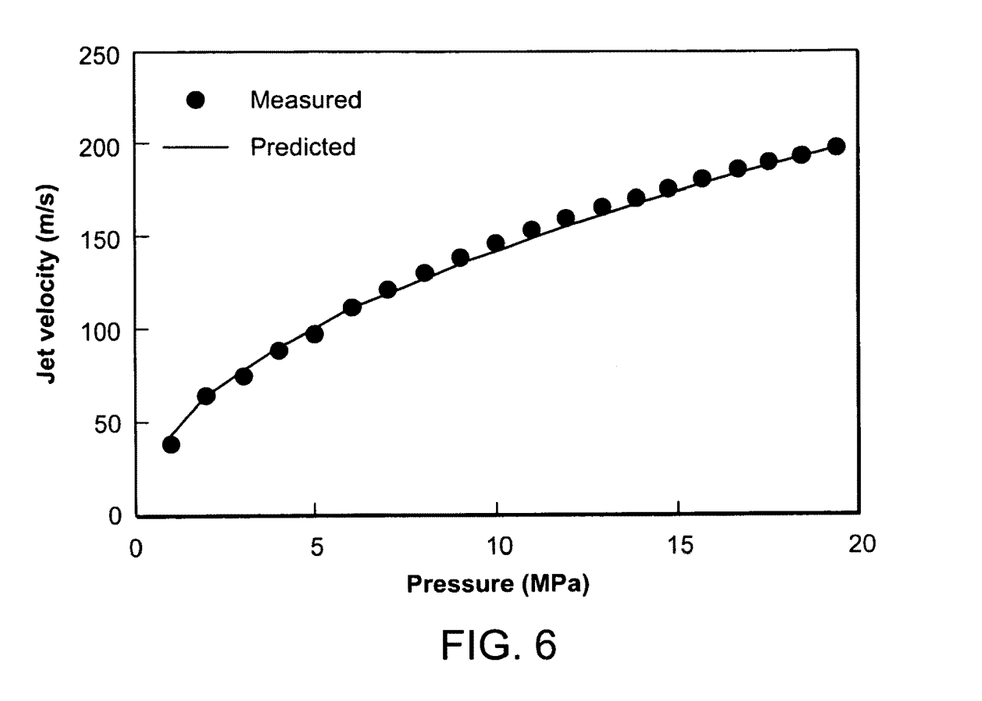
FIG. 6 is a graph showing measured and predicted jet velocity of one embodiment of a needle-free injector.

By taking repeated voltage step response measurements (increasing the voltage step in 10 V increments up to 200 V) and fitting to the steady state piston velocity (t>20 ms), the steady-state jet velocity was computed and then plotted against pressure as shown in FIG. 6. FIG. 6 confirms the modeled predictions of the Bernoulli equation and demonstrates that the needle-free injector device 200 is capable of generating the jet velocities that are required for effective jet delivery. It can be understood that the voltage step response and piston velocity can be varied as needed.

Figure 7:
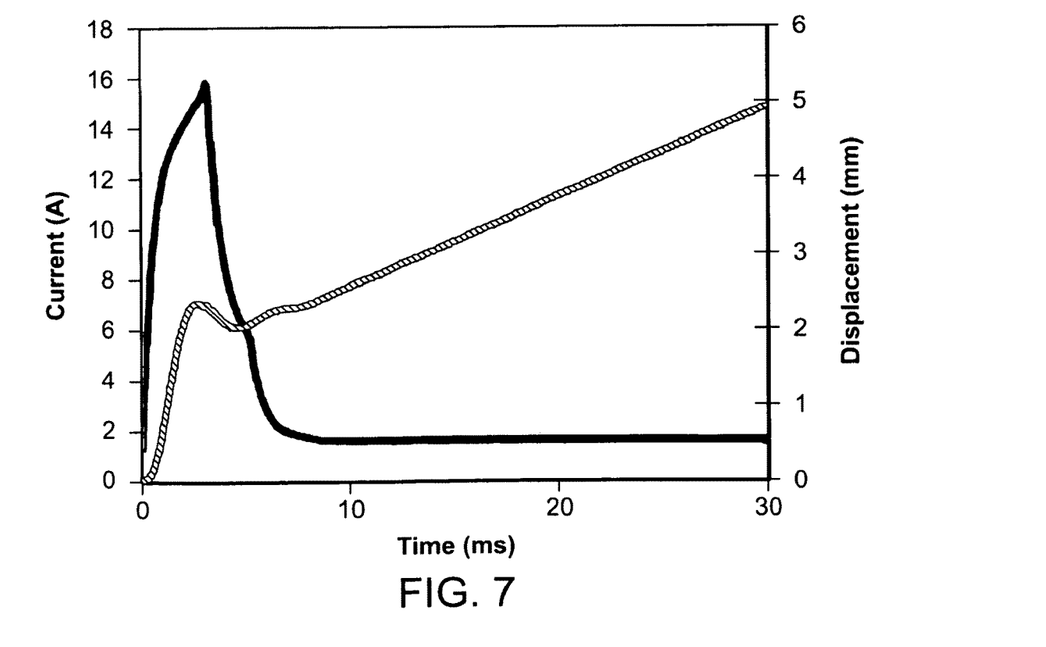
FIG. 7 is a graph showing the current and displacement responses for delivery with one embodiment of a needle-free injector.

The open-loop repeatability of the needle-free injector system 200 was tested by using a shaped voltage waveform to eject a nominal volume of 50 µl. The voltage waveform consisted of an initial pulse (180 V, 3 ms) to penetrate the skin surface, followed by a follow-through pulse (20V, 30 ms) to obtain the total required volume of delivery. The injector 200 was fired four times per syringe refill, 100 times in total. The current and displacement waveforms (averaged over 100 repetitions) are shown in FIG. 7.

Using this waveform, the volume of fluid delivered per shot was 50.9±1 µL (mean±sd, n=100). This repeatability is similar to that claimed by commercial jet injectors, and can be further enhanced through the used of closed-loop position control. The repeatability of the 50 µL injection, is thus ±1 µL.

Figure 8A:
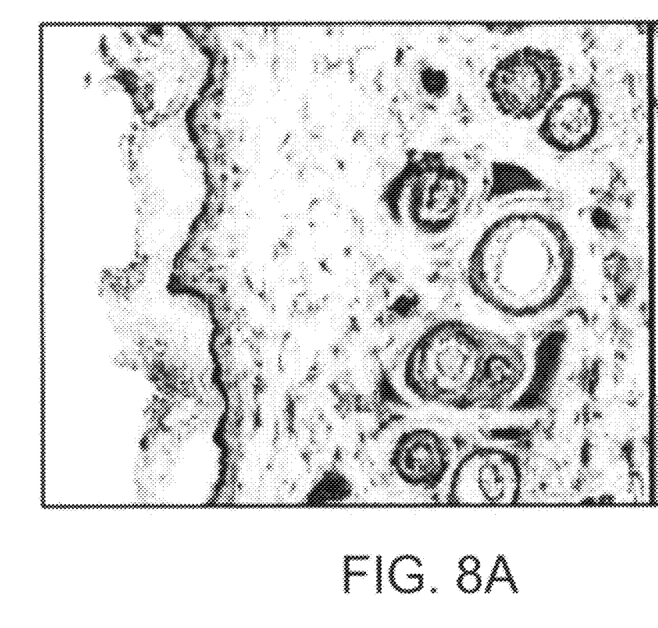
FIGS. 8A and 8B show the result of dye injected into pig tissue with one embodiment of a needle-free injector.
Figure 8B:
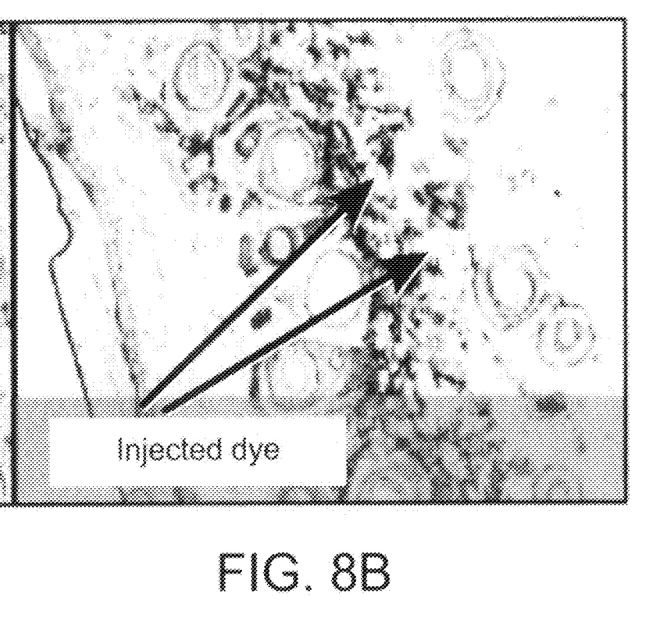

The efficacy of the needle-free injector device 200 for drug delivery was tested in the following manner. A voltage waveform was designed (140 V, 1.5 ms, followed by 20 V, 10 ms) to eject a nominal 10 µL quantity of fluid. Upon establishing the repeatability of the ejected volume, the injector 200 was used to inject red tissue marking dye (Polysciences Inc, Warrington, Pa.) into post-mortem guinea-pig skin. The tissue was then counterstained with Mayer's Hematoxylin (Dako-Cytomation, Glostrup, Denmark). FIG. 8A and FIG. 8B contrast non-injected and injected tissue showing that during this delivery, the injected dye has effectively reached the targeted lower dermis.

A significant advantage offered by the voice-coil motor used in the needle-free injector device 200 is the ability to servo-control the motor force, pressure or displacement in real time. This allows real-time feedback control of pressure and volume of drug delivery, and permits the device to tailor delivery to the drug type or injection site.

In one embodiment, a closed-loop control system consisting of a compact switching amplifier is controlled by a microprocessor. In an additional or alternative embodiment, the addition of a force transducer to the moving coil allows the device to be used as a dynamic material analyzer. Non-linear system identification techniques are used to interrogate the properties of the tissue prior to injection, allowing the device to customize an injection waveform appropriately for the tissue.

One advantage of using a needle-free injector device with a controllable linear Lorentz-force actuator is control of injector pressure. This actuator allows rapid control of the injection pressure during injections. Using this device, precise control over delivery parameters can be achieved.

Lorentz force actuators, for example, can enable high pressure and velocity at the start of the injection cycle, and low to medium velocity and pressure to deliver the majority (or all) of the dose, and then a slightly higher force at the tail end of the cycle to better ensure that all of the drug is delivered.

Advantageously and in addition, the control of force and velocity means that one can maintain constant pressure and force through the whole second stage delivery cycle (first stage being the breaking of the skin with higher force/velocity/pressure). Through studies conducted utilizing the needle-free injector with the Lorentz-force Actuator, it is known that the majority of delivery of fluid occurs during the second stage. The lower pressure follow through does not appreciably affect the depth of penetration. The advantage of using a Lorentz-force driven injector is that one can better ensure that all of the drug is delivered, compared to other needle-free fixed force gas or spring systems, wherein by their nature, there can be a progressively declining force/pressure/velocity as the delivery cycle progresses. The problem with this declining force/velocity is the resulting wet injections whereby there is insufficient pressure/velocity at the end of the stroke of the piston to force/inject all of the drug. The consequence is that some of the drug/dose is left on the outside of the skin (or even perhaps in the vial.) One possible counter to this with gas or spring is to provide much greater force/velocity than is necessary. This can, however, lead to delivery at a depth that is greater than is desired as well as the possibility of pain and potential tissue damage considerations. Thus, the use of a Lorentz-force actuator and voice-coil motor allows for greater control of injection as well as depth of injection, and thus the potential for more optimal delivery of a drug with the possibility of less pain and possible decrease of potential injury to tissue.

Experiments on injection dispersion into porcine tissue show that the primary injection depth is determined by the initial peak pressure and the majority of fluid delivery occurs during the follow-through or second pressure period. Thus, in order to deliver less or more fluid to a certain depth in tissue, the needle-free injector can be controlled or programmed to either shorten, lengthen, or vary the follow-through pressure but does not necessarily vary the initial peak pressure.

There may be further optimization of the follow-through pressure that can be explored in the future. It is possible that a pressure lower than the initial peak pressure can still have enough jet power to affect the depth of the injection. In the experiments conducted with the Lorentz-force injector, the maximum follow-through pressure to inject the drug was only 33% of the peak pressure. It can be understood that in certain circumstances, the follow-through pressure can be 10-100% of the peak pressure.

Future experiments could focus on finding the maximum follow-through pressure that would not affect injection depth. In summary, maximizing the follow-through pressure could allow for faster injections since more fluid could be delivered in a shorter period of time. The presented Lorentz-force injector allows for this type of control.

The depth of injection can be varied based on changing the peak pressure with which the fluid is ejected. Since jet power is proportional to pressure, increasing the pressure increases the jet power. These results agree with known Schramm-Baxter observations that the depth of injection increases with increasing jet power. As described by O. A. Shergold, et al., "The Penetration of a Soft Solid by a Liquid Jet, with Application to the Administration of a Needle-Free Injection," *J. Biomech.*, 39 (14):2593-2602 (2006), in, the mechanical properties of the tissue affect the ability of the jet to penetrate, so it can be expected that different quantitative models are necessary for different tissue sources.

Many drugs are best delivered to a target depth. Some are designed to be injected into muscle tissue, while on the other end of the spectrum there are very strong arguments to suggest that most—if not all—vaccines are best delivered to the intra-dermal layer (relatively shallow depth). It has recently been postulated that if vaccines could be delivered accurately to the intra-dermal layer, the enhanced immune response (as a result of delivering in closer proximity to the Dendritic Cells and even more specifically the Langerhan cells), could possibly result in the a substantial decrease in the amount of the 'active' that would be needed for an efficacious injection/therapy.

It has also been postulated that the amount of active substance needed (by delivering to a specific depth) might be able to be reduced by between 50% and 90%. As such, the ability to control the parameters of a needle-free injector system, and control depth, can have very significant impact on the cost of drugs and vaccines. In addition, if one could reduce the amount of active substance needed, the size/capacity of production plants could be reduced, thus resulting in more accuracy, and more relevance in production. Further, the number of doses that could be produced from any one pharmaceutical, biological, and vaccine production plant may be able to be doubled or possibly even increased 3-10 fold. In addition, if one could reduce the amount of active substance needed, the size and capacity of production plants could be reduced.

Additionally, control of force and velocity can enable both high velocity to break through the skin and then a lower level of force (velocity) to deliver the drug. Advantageously, this may help prevent the shearing or degradation of the tissue into which the drug, molecule, biological, or vaccine is injected.

Operation of the needle-free injector 200 is relatively simple. When fired, a pressure source applies a force to the piston. The piston transmits this force to the drug in an injection cylinder. As most aqueous solutions are essentially incompressible, the pressure of the drug rises. The drug is forced through the orifice of the nozzle and ejected at a speed related (but not strictly proportional, due to turbulence, etc.) to the force on the piston and the diameter and shape of the orifice. If the speed of the ejected drug is sufficient and the nozzle is of the proper diameter, it will breach the skin of the recipient and penetrate to a depth related (but again not proportional) to the speed of the drug and the mechanics of the skin.

As previously stated, it is hypothesized that controlling the pressure profile of the injector is a means of controlling the depth and shape of the injection. Such techniques allow for more precise control over delivery. Generating a variable pressure profile injector can be achieved by generating a variable force to drive the injector's piston. Conventional needle-free injectors, powered by springs or compressed gas, are difficult to control in such a manner. Electrical control allows control of the injector system in real time. Thus, the preferred device uses a Lorentz-force actuator or voice-coil motor for driving a variable-pressure needle-free injector, and has an output force that is proportional to an electrical current.

In general, the needle-free injector device is comprised of many components, but can be broken down into three major blocks; a housing and motor structure, injection cylinder, and an autoloader (which will be described in FIGS. 9 and 10.) The injector device is designed to deliver 100 μL volume at 60 MPa.

The housing and motor structure provides a support onto which the rest of the needle-free injector device is attached. It is built around a BEI Kimco Magnetics linear Lorentz-force motor, and provides a constrained, linearly-actuated main shaft to which the piston and a cylinder assembly is connected.

The coil of the motor structure is attached to a 6.35 mm diameter nonmagnetic stainless steel main shaft that runs the length of the motor and protrudes from the front edge of the coil structure. Linear ball bearings inserted into the 12.7 mm diameter race inside the linear motor housing constrain the main shaft.

An axial-misalignment coupling is attached to the front end of the main shaft. This coupling is designed such that the linear force is transmitted between the device's main shaft and the piston (part of the piston and cylinder assembly), but off-axis forces do not cause binding. Thus, the piston and cylinder assembly can be slightly off-axis without appreciably affecting performance.

Figure 9:
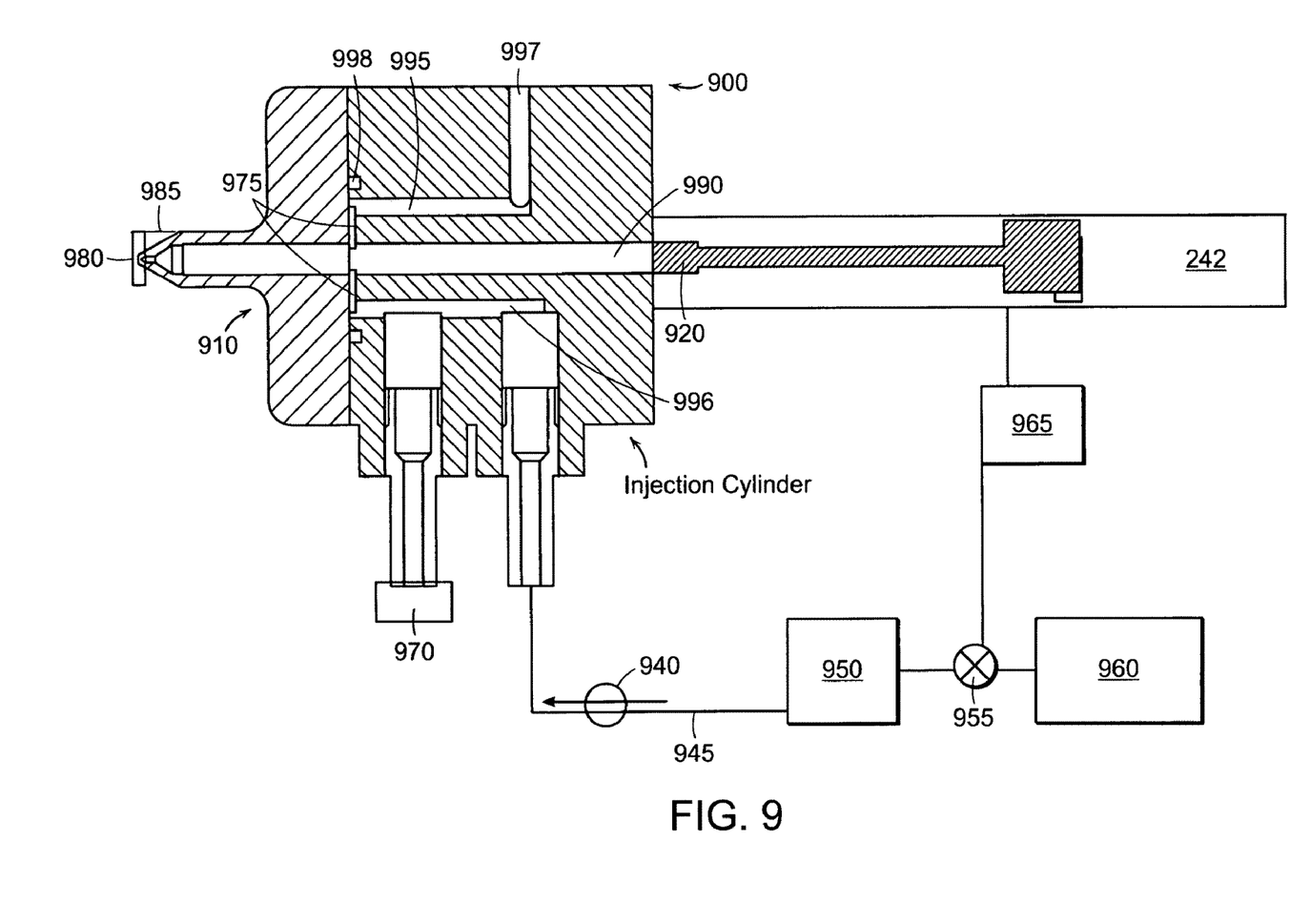
FIG. 9 shows one embodiment of a cylinder of a needle-free injector device.

An embodiment of an injection cylinder configured for autoloading of the needle-free injector device is shown in FIG. 9. The cylinder can be machined out of a single block of Type 303 stainless steel. The cylinder 900 allows for bleeding, autoloading, and pressure sensing.

A central bore 990 runs the length of the cylinder 900. The central bore 990 can act as a chamber for holding a substance. Alternatively, or in addition, the cylinder 900 can include a vial, a syringe, or any means of holding the substance within the cylinder 900.

The cylinder 900 further includes an upper auxiliary bore 995 and a lower auxiliary bore 996. The upper and lower auxiliary bores are connected to the central bore 990 by a milled channel on the cylinder face between all three passages 975.

The lower auxiliary bore 996 mounts a check valve 940 and a pressure sensor or pressure transducer 970. The pressure sensor 970 monitors the pressure inside the injection cylinder 900 in real time. The central bore 990 is the guide for the piston 920.

In this embodiment, the piston 920 of the device is a commercially available syringe piston, a Hamilton model #50495-35. These pistons fit the bore of the cylinder 900 on one end, and the misalignment coupler inside the housing/motor structure on the other. The piston 920 can alternatively be any suitable piston.

A ring is milled into the cylinder face to accept an O-ring 998 that seals the nozzle to the cylinder. The O-ring 998 encompasses all of the high-pressure passageways on the front face of the cylinder 900. A six-bolt hole pattern is drilled and tapped into the front cylinder face. These bolts hold a nozzle 910 against the cylinder 900.

The cylinder 900 further includes a bleed port 997. The bleed port 997 forces air that may be trapped in the injector device to be evicted. In operation, the bleed port 997 is opened and the injector device is loaded with a liquid. When all of the air has escaped, (evident when bubbles cease to escape in the liquid), the bleed port 997 is closed.

In one embodiment, the check valve 940 is an automotive style poppet valve. An O-ring that is approximately 3 mm in diameter (not shown) is located just beneath the valve head to provide additional sealing capacity. The O-ring seals the valve at low back-pressure, while at high back-pressure, the metal lip of the poppet valve seals against a valve seat of the check valve 940 (not shown). The check valve 940 has a cracking pressure of approximately 275 kPa and is used in the autoloading process to refill the injection cylinder 900 automatically. The check valve 940 may alternatively be any other type of suitable valve.

The front of the cylinder 900 is drilled and tapped for the nozzle 910. Each nozzle 910 is constructed of aluminum, and has a 100 μm nozzle in the end.

The front of nozzle 910 has a flip-cap 980 attached to it. The flip-cap 980 is attached to the nozzle body by a hinge 985. The flip cap 980 can alternatively be attached to the nozzle by any suitable means. It works to seal an orifice of the nozzle 910 during autoloading to avoid air entering the device during autoloading. It clamps over the nozzle 910 and seals it with a silicone rubber seal when the injector is not in use, or during autoloading. The flip-cap 980 is then opened in order to inject the drug out of the nozzle 910. The flip-cap 980 can be operated automatically by a controller.

The check valve 940 is in communication with a drug reservoir 950 within which a medicament to be injected is stored. The drug reservoir 950 is designed to be easily replaceable. In one embodiment, the reservoir 950 is a standard 50 mL medical vial and holds enough drug for 500 injections. Alternatively or in addition, drug reservoirs for holding various amounts of medicament may be used.

The drug reservoir 950 is in further communication with an additional valve 955. The valve 955 is preferably a solenoid valve which is a Mead Fluid Dynamics V1A04-BW1 three-port device. Internally, the valve 955 connects an output passageway to one of two input passages. The valve 955 may alternately be any type of suitable valve.

In one embodiment, the drug reservoir 950 is connected to the output passageway of the valve 955 and a pressure reservoir 960 is connected to an input of valve 955. The pressure reservoir 960 is a high-pressure argon tank with a regulator. Alternatively or in addition, any suitable pressure source may be used. Alternatively, the substance to be injected can be drawn into the cylinder 900 with the motor 242. Thus, pressure may or may not be used to push the substance from the drug reservoir 960.

The pressure reservoir 960 is connected via the valve 955 to the air space or dead volume above the drug in the drug reservoir 950. A dip tube 945 that reaches the bottom of the drug reservoir is also connected to the check valve 940 in the injection cylinder 900.

During the autoloading process, the valve 955 is opened, thus applying pressure to the drug reservoir 950 from the pressure reservoir 960. Drug is therefore, forced up the dip tube 945, through the check valve 940, and into the central bore 990 for injection. The piston 920 is slowly drawn back using the position sensor 260 (shown in FIG. 2) as a reference to allow the cylinder 900 to fill without creating bubbles or cavitation. Advantageously, autoloading allows the injector to be automatically reloaded after each injection. A controller 965 can be used to automate the autoloading process by controlling the motor 242 and the valve 955.

Further, the position sensor can advantageously monitor the location of the piston 920 inside the injection cylinder 900, while the pressure sensor 970 monitors pressure inside the injection cylinder 900 in real time. These sensors, combined with data from the voice-coil motor 242 parameters, can be used to gauge the effectiveness of each injection. With a fast enough processing system, these sensors can be used to monitor and correct any errors in real time to produce a proper injection every time if skin parameters are known.

Therefore, the needle-free injector device allows for both automatic and controlled injections and well as automatic or autoloading capability.

Figure 10:
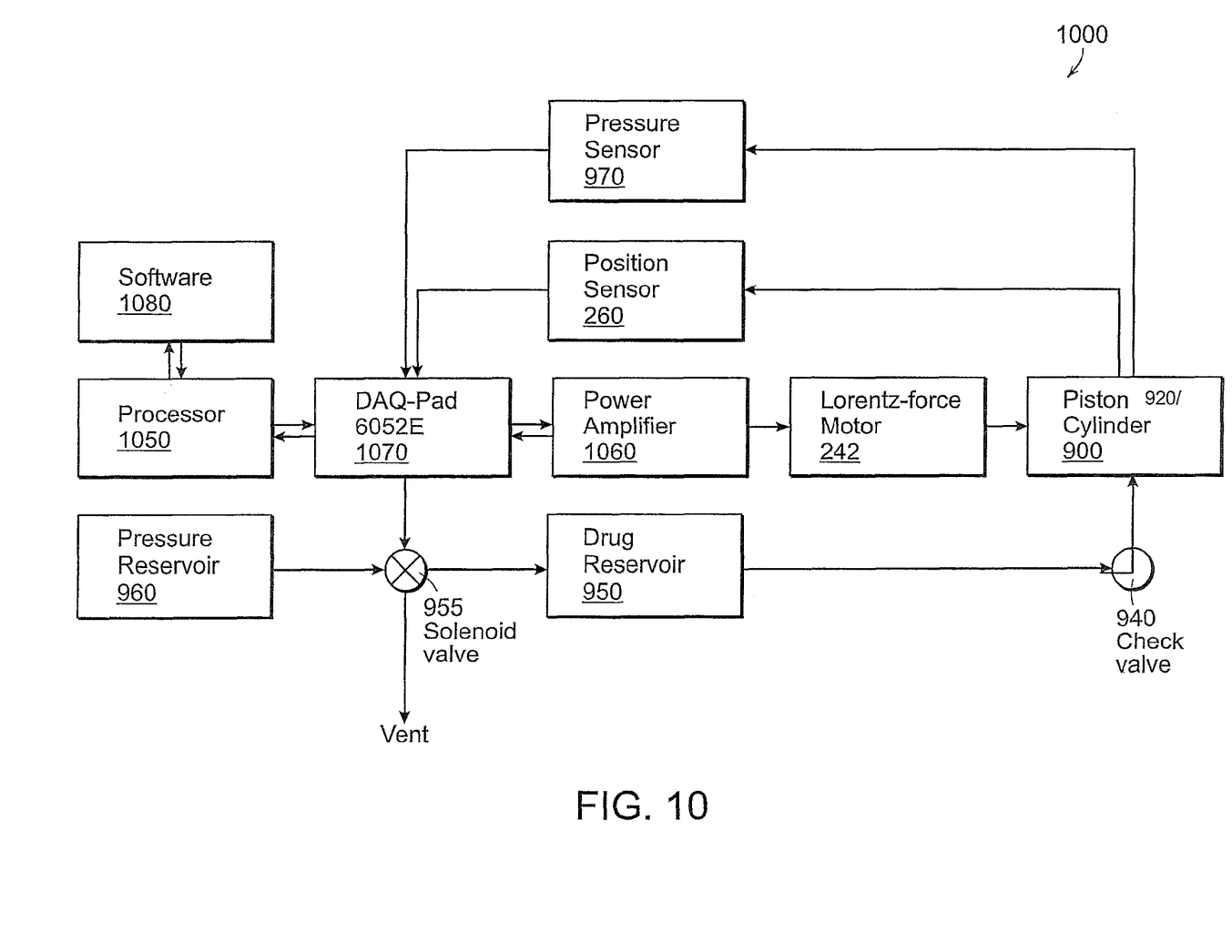
FIG. 10 is a flow diagram showing the process of controlling and autoloading one embodiment of a needle-free injector.

A block diagram of the injector device can be seen in FIG. 10. The injector device is controlled by a linear amplifier 1060, a computer interface 1070, and a processor 1050.

The peak forces involved in needle-free drug delivery require a significant amount of energy delivered over a very short period of time. It is important that the pressure in the injection cylinder quickly rise to pressures capable of breaching tissue, or much of the drug will be lost before it can penetrate. Therefore, the source driving the motor should be capable of producing much higher voltages than are needed to produce peak force, so that pressure rise times can be minimized.

The Lorentz-force motor 242 is driven by a 4 kW (peak, into 4Ω) commercial linear audio power amplifier 1060, an AE Techron model LVC5050. The amplifier 1060 is driven with a National Instruments DAQPad-6052E data acquisition device 1070, which also controls an autoloader solenoid valve 955 and monitors the injector device's sensors including both the position sensor 260 and the pressure sensor 970.

The 6052E's IEEE-1384 interface 1070 is connected to the processor 1050, that, in conjunction with the Injector Control software 1080, generates the firing waveforms and controls the autoloading sequence. The injector software 1080 is written in the C# language of Microsoft Visual Studio NET 2003.

The Injector Control software 1080 allows the user to purge, autoload, and fire the injector while monitoring its output subsequent to each injection on a laptop. In addition, it provides a static bias current to hold the piston in a retracted position. It also provides a piston stabilization feature designed to prevent piston creep when the injector is not resting horizontally, and a pressure tail-off algorithm designed to brake the piston post-injection and keep the falling pressure from leaking excess drug out the nozzle.

The injector is fired with open-loop computer control. A drive waveform file (a column of output voltages) is read from the laptop's disk. This waveform is checked for validity, and then output via the needle-injector device. The needle-injector device monitors and logs the injector device's sensors during the injection.

The injector autoloads under full real-time feedback control. When the autoload command is given, a solenoid valve 955 in the autoloader 1000 is opened, allowing pressurized drug from a drug reservoir 950 to reach the internals of the injection cylinder 900. Then, the piston 920 is slowly drawn backwards in small steps, using the position sensor 260 as a reference. The processor 1050 monitors movement and modulates the drive power accordingly, as the friction between the injection cylinder 900 and the piston is nonuniform over the travel of the piston. When the piston 920 has fully retracted, both the autoloader pressure and coil drive of the Lorentz-force motor 242 are shut off. The autoloading capability allows for repeatability and accuracy of autoloading the desired amount of drug to an accuracy of ±1 μL.

The position assist function is a separate thread that runs a real-time feedback control loop on piston position via the position sensor and modulates the bias power of the coil to achieve a steady piston position irrespective of gravitational forces or acceleration of the device as it is moved. Thus, the injector can be held vertically without bleed from the nozzle due to gravity.

Using this system, it is possible to design custom injection pressure profiles for different situations. The pressure profiles are related, although nonlinearly, to the force provided by the linear motor on the cylinder piston, and therefore to the current running through the motor coil. The pressure and force are not linear due to second order effects, such as resonances in the complaint components (Teflon piston tip, O-rings, possibly the pressure transducer head). However, the force and coil current are directly proportional to one another.

Thus, pressure profiles are created by modifying the input waveform file, a simple task with the Injector Control software. Primarily, the pressure profiles produced consist of a 2 to 3 ms "follow through" of 10 to 20 MPa. By changing the voltages in the waveform, profiles can be created to damp out resonances. Over time, a library of waveforms are created, each corresponding to a different set of desired parameters.

In summary, the waveforms are created to drive the Lorentz-force coil in order to create the desired injection parameters. The desired parameters include a variety of peak injection powers and a variety of follow through injection powers. Through the software control of the Lorentz-force jet injector, each of these injection pressure profiles can be saved and then recalled for use by opening the saved voltage waveform file.

What has been described is a needle-free injector with an actuator that is optimized to provide high instantaneous force (>200 N) and power (4 kW) while still allowing a total stroke of about 25 mm. The stroke length can however be varied to the desired amount. The actuator is relatively inexpensive, compact, and lightweight, allowing it to serve as the force generator in a portable, reusable, handheld NFI system. The actuator is capable of accelerating liquid drug in quantities of up to 250 μL to a speed of more than 200 ms$^{-1}$. The repeatability of a 50 μL volume ejection is better than ±1 μL. In other embodiments, actuators are capable of accelerating substances in quantities of between 10 μL and 40 milliliters to a speed of between 50 ms$^{-1}$ and 1500 ms$^{-1}$.

The needle-free injector device as described is an optimal platform for jet mechanics studies. It is completely modular, nearly completely automatic, and offers a great amount of flexibility in control of pressure profiles. Automatic loading and firing allows rapid, repeatable experimentation. In general, it can be understood that any and all parameters presented herein have been experimental and variations in any and all presented parameters and conditions are possible.

With the knowledge of what is achievable using the Lorentz-force actuator in these injectors, it is believed the device can be used effectively on humans and animals. The needle-free injector device can be used as a platform for a next-generation, commercially viable device incorporating a custom voice-coil and an integrated power supply and real-time feedback control of the entire device to increase repeatability further. It is expected that such a device will be an excellent tool for fast, mass immunizations.

While this invention has been particularly shown and described with references to preferred embodiments thereof, it will be understood by those skilled in the art that various changes in form and details may be made therein without departing from the scope of the invention encompassed by the appended claims.

What is claimed is:

1. A needle-free transdermal transport device for transferring a substance across a surface of a biological body comprising:
    a chamber for holding the substance;
    a nozzle in fluid communication with the chamber;
    a drug reservoir for storing the substance to be transferred to the chamber; and
    a controllable electromagnetic actuator in communication with the chamber, the actuator comprising a moving coil assembly and a stationary magnet, the actuator receiving an electrical input and generating in response a force, the force causing a needle-free transfer of the substance from the chamber and to the biological body and being variable responsive to variations in the electrical input during actuation, the actuator drawing the substance from the drug reservoir and being precisely controlled to move the substance to the chamber.

2. The device of claim 1, further comprising a pressure source for automatically pressurizing the substance in the drug reservoir to transfer it from the drug reservoir into the chamber.

3. The device of claim 1, wherein variations in the received electrical input correspond to feedback.

4. The device of claim 1, wherein the controllable electromagnetic actuator is bi-directional, generating a positive force responsive to a first electrical input and a negative force responsive to a second electrical input.

5. The device of claim 1, wherein the electromagnetic actuator forces the substance through the nozzle and produces a jet having sufficient velocity to pierce the surface of the biological body.

6. The device of claim 1, further comprising a rechargeable power source, used in production of the electrical input.

7. The device of claim 1, further comprising a check-valve between the drug reservoir and the chamber.

8. The device of claim 1, further comprising a pressure sensor for sensing the pressure inside the chamber.

9. The device of claim 1, further comprising a piston for pushing the substance out of the nozzle for delivery.

10. The device of claim 9, further comprising a position sensor for monitoring the position of the piston within the needle-free transdermal transport device.

11. The device of claim 10, further comprising a processor, that automatically tailors the position of the actuator according to feedback from the position sensor.

12. The device of claim 1, further comprising a servo-controller in electrical communication with the controllable electromagnetic actuator, the servo-controller providing the electrical input.

13. The device of claim 1, wherein the device is adapted to provide a plurality of independent needle-free transfers, each transfer occurring in rapid succession with respect to a preceding transfer.

14. The device of claim 1, further comprising an automatically controlled flip-cap on the nozzle, the flip cap closing during loading the chamber with the substance and opening during injection of the substance.

15. A needle-free transdermal transport device for transferring a substance across a surface of a biological body comprising:
    a chamber for holding the substance;
    a nozzle in fluid communication with the chamber;
    a piston for automatically driving the substance out of the nozzle for injection;
    a position sensor for automatically sensing the position of the piston within the needle-free device; and
    a controllable actuator in communication with the chamber, the actuator comprising a moving coil assembly and a stationary magnet, the actuator receiving an electrical input and generating in response a force, the force causing a needle-free transfer of the substance between the chamber and the biological body and being variable responsive to variations in the electrical input during actuation, and the actuator further being controllable in response to feedback provided by the position sensor.

16. The device of claim 15, further comprising a drug reservoir for storing the substance.

17. A method for transferring a substance across a surface of a body comprising:
    drawing the substance from a drug reservoir with a controllable electromagnetic actuator comprising a moving coil assembly and a stationary magnet, the drawing being precisely controlled to move the substance to a chamber of a needle-free injector;
    applying an electrical input to the actuator;
    producing with the actuator a mechanical force corresponding to the electrical input; and
    applying the mechanical force to the chamber coupled at one end to a nozzle, the mechanical force producing a pressure within the chamber, the force causing a needle-free transfer of the substance from the chamber to the biological body and the force being variable responsive to variations in the electrical input during actuation.

18. A method for transferring a substance across a surface of a body comprising:
    sensing the position of a piston within a cylinder of a needle-free injector;
    applying an electrical input to a controllable electromagnetic actuator comprising a moving coil assembly and a stationary magnet;
    producing with the actuator a mechanical force corresponding to the electrical input; and applying the mechanical force to a chamber coupled at one end to a nozzle, the mechanical force producing a pressure within the chamber, the force causing a needle-free transfer of the substance from the chamber to the biological body, the force being variable responsive to variations in the electrical input during actuation, and the actuator being further controllable according to feedback provided by a position sensor.

19. The method of claim 18, further comprising a drug reservoir for storing the substance.

* * * * *